United States Patent
Engqvist (10) Patent No.: US 9,486,527 B2
(45) Date of Patent: Nov. 8, 2016

(54) COMPOSITION FOR SUSTAINED DRUG DELIVERY COMPRISING GEOPOLYMERIC BINDER

(75) Inventor: Hakan Engqvist, Osthammar (SE)

(73) Assignee: EMPLICURE AB, Uppsala (SE)

( * ) Notice: Subject to any disclaimer, the term of this patent is extended or adjusted under 35 U.S.C. 154(b) by 0 days.

(21) Appl. No.: 13/319,201

(22) PCT Filed: May 7, 2010

(86) PCT No.: PCT/GB2010/000910
§ 371 (c)(1),
(2), (4) Date: Apr. 27, 2012

(87) PCT Pub. No.: WO2010/128300
PCT Pub. Date: Nov. 11, 2010

(65) Prior Publication Data
US 2012/0252845 A1    Oct. 4, 2012

(30) Foreign Application Priority Data

May 8, 2009 (SE) .................................. 0900626
Feb. 8, 2010 (SE) .................................. 1000117

(51) Int. Cl.
A61K 47/02    (2006.01)
A61K 9/16     (2006.01)
A61K 31/4468  (2006.01)

(52) U.S. Cl.
CPC ............ *A61K 47/02* (2013.01); *A61K 9/1611* (2013.01); *A61K 31/4468* (2013.01)

(58) Field of Classification Search
None
See application file for complete search history.

(56) References Cited

U.S. PATENT DOCUMENTS

| | | |
|---|---|---|
| 4,861,599 A | 8/1989 | Springolo et al. |
| 5,318,779 A | 6/1994 | Hakamatsuka et al. |
| 5,443,812 A | 8/1995 | Nakajima et al. |
| 5,902,591 A | 5/1999 | Herstein |
| 6,123,925 A * | 9/2000 | Barry et al. ............ 424/49 |
| 6,334,856 B1 | 1/2002 | Allen et al. |
| 6,342,249 B1 | 1/2002 | Wong et al. |
| 6,503,231 B1 | 1/2003 | Prausnitz et al. |
| 6,635,281 B2 | 10/2003 | Wong et al. |
| 6,767,557 B2 | 7/2004 | Ulrich et al. |
| 2002/0122828 A1 | 9/2002 | Liu |
| 2003/0096002 A1 | 5/2003 | Borek et al. |
| 2003/0118641 A1 | 6/2003 | Maloney et al. |

(Continued)

FOREIGN PATENT DOCUMENTS

| | | | |
|---|---|---|---|
| CN | 101104080 | * | 1/2008 |
| CN | 101104080 A | * | 1/2008 |

(Continued)

OTHER PUBLICATIONS

Machine translation of CN 101104080 A, Dou et al., Jan. 16, 2008.*

(Continued)

*Primary Examiner* — Carlos Azpuru
*Assistant Examiner* — Casey Hagopian
(74) *Attorney, Agent, or Firm* — Ryan Kromholz & Manion, S.C.

(57) ABSTRACT

The present invention relates to a sustained release medical composition comprising an active pharmaceutical ingredient and a geopolymeric binder. Preferably the active pharmaceutical ingredient is combined with the geopolymeric binder during the formation of that binder.

20 Claims, 3 Drawing Sheets

(56) References Cited

U.S. PATENT DOCUMENTS

| | | |
|---|---|---|
| 2005/0163856 A1 | 7/2005 | Maloney et al. |
| 2005/0273046 A1 | 12/2005 | Kwiatkowski et al. |
| 2006/0024358 A1 | 2/2006 | Santini, Jr. et al. |
| 2006/0057206 A1 | 3/2006 | Wong et al. |
| 2006/0165787 A1 | 7/2006 | Moerck et al. |
| 2007/0053986 A1 | 3/2007 | Kuhn et al. |
| 2007/0123837 A1 | 5/2007 | Adachi et al. |
| 2007/0151485 A1 | 7/2007 | Hermansson et al. |
| 2007/0212414 A1 | 9/2007 | Baichwal et al. |
| 2007/0224129 A1 | 9/2007 | Guimberteau et al. |
| 2007/0248656 A1* | 10/2007 | Galer .................. 424/448 |
| 2007/0292526 A1 | 12/2007 | Barbe et al. |
| 2008/0063725 A1 | 3/2008 | Guimberteau et al. |
| 2008/0107720 A1 | 5/2008 | Walters et al. |
| 2009/0200262 A1 | 8/2009 | Scholten et al. |

FOREIGN PATENT DOCUMENTS

| | | |
|---|---|---|
| EA | 010826 | 12/2008 |
| EP | 265061 | 4/1988 |
| EP | 336014 | 6/1992 |
| EP | 947489 | 10/1999 |
| EP | 1674094 | 6/2006 |
| EP | 1285655 B1 | 5/2007 |
| EP | 2100850 | 9/2009 |
| EP | 1429819 | 11/2010 |
| GB | 2307862 | 6/1997 |
| JP | H02268104 | 11/1990 |
| JP | H07-188000 | 7/1995 |
| JP | 9030988 | 2/1997 |
| WO | WO89/05632 | 6/1989 |
| WO | WO01/72663 | 10/2001 |
| WO | WO03/090729 | 11/2003 |
| WO | WO03/092785 | 11/2003 |
| WO | WO2004/024224 | 3/2004 |
| WO | WO2004/028577 | 4/2004 |
| WO | WO2004/040036 | 5/2004 |
| WO | WO2004/058194 | 7/2004 |
| WO | WO2005/037268 | 4/2005 |
| WO | WO2005/039508 | 5/2005 |
| WO | WO2005/051358 | 6/2005 |
| WO | WO2006/000229 | 1/2006 |
| WO | WO2006/017336 | 2/2006 |
| WO | WO2006/083904 | 8/2006 |
| WO | WO2006/089843 | 8/2006 |
| WO | WO2006/096544 | 9/2006 |
| WO | WO2007/074349 | 7/2007 |
| WO | WO2008/080109 | 7/2008 |
| WO | WO2008/105737 | 9/2008 |
| WO | WO2008/105738 | 9/2008 |
| WO | WO2008/105739 | 9/2008 |
| WO | WO2008/118096 | 10/2008 |
| WO | WO2008/142572 | 11/2008 |
| WO | WO2009/113856 | 9/2009 |
| WO | WO2010/096704 | 8/2010 |

OTHER PUBLICATIONS

Duxson et al., Geopolymer technology: the current state of the art, J Mater Sci, 42, 2917-2933, (2007).*
"Breast Cancer", American Cancer Society. Accessed online at www.cancer.org on Jan. 26, 2014, pp. 1-133.*
Price et al., In-vitro release characteristics of tetracycline HCl< khellin and nicotinamide adenine dinecuieotide . . . J Microencapsulation, vol. 18, No. 6 713-722 (2001).
Levis et al, Use of coated microtubular halloysite for the sustained release of diltiazem hydrochloride and propranolol hydrochloride, Int. J. Pharm, 253, 145-147 (2003).
Lasserre et al., Ceramic Drug-Delivery Devices, Critical Reviews in Therapeutic Drug Carrier Systems, 15(1):1-56, (1998).
Byrne et al., Use of porous aluminosilicate pellets for drug delivery, J Microencapsulation, Jun. 2005: 22(4): 423-437.
Rimoli et al., Synthetic zeolites as a new tool for drug delivery, J Biomed. Mater, Res., 87A, 156-164, (2008).
Cavallaro et al., Drug Delivery Devices Based on Mesoporous Silicate, Drug Delivery, 11:41-46, 2004.
Itokazu et al., Development of porous apatite ceramic for local delivery of chemotherapeutic agents, J. Biomed. Mater. Res., 39, 536-538 (1998).
Netz et al., Potential use of gelcasting hydroxyapatite porous ceramic as an implantable drug delivery system, Int. J. Pharmaceutics, 213, 117-125, (2001).
Krajewski et al., Porous Ceramic bodies for drug delivery, J Mat. Sci, Materials in Medicine, 12, 763-771, (2000).
Yao et al., Fabrication of hydroxyapatite ceramics with controlled pore characteristics by slip casting. J of Materials Science: Materials in Medicine, 16, 161-165, (2005).
Komlev et al., Porouse hydroxyapatite ceramics of bi-modal pore size distribution, J Materials Science: Materials in Medicine, 13, 295-299, (2002).
Byrne et al., Use of commerical porous ceramic particles for sustained drug delivery, Int. J. Pharmaceutics, 246, 61-73, (2002).
Gbureck et al., Low temperature direct 3D printed bioceramics and biocomposites as drug release matrices, J Controlled Release, 122, 173-180 (2007).
Medvecky et al., Study of Controlled Tetracycline Release from Porous Calcium Phosphate/Polyhydroxybutyrate Composites, Chem Pap, 61(6), 477-484, (2007).
Paul et al., Tricalcium Phosphate Delayed Release Formulation for Oral Delivery of Insulin: A Proof-of-Concept Study, J Pharm Sci, vol. 97, No. 2, Feb. 2008.
Stevenson et al., Relationships between composition, structure and strength of inorganic polymers, J of Mater Sci, 40, 2023-2036, 2005.
Zoulgami et al., Synthesis and physico-chemical characterization of a polysialate-hydroxyapatite composite for potential biomedical application, Eur Phys J AP, 19, 173-179, 20.
Zheng et al., Preparation of geopolymer precursors by sol-gel method and their characterization, J Mater Sci, 44, 399103996, 2009.
De Silva et al. "The role of $Al_2O_3$, $SiO_2$ and $Na_2O$ on the Amorphous . . . " Journal of the Australian Ceramic Society, vol. 45[1], 2009, 63 to 71.
Extract from "Handbook of Pharmaceutical Excipients" 4th edition, Rowe et al (eds.), 2003, pp. 89-92.
Chrétien M.N., "Supramolecular photochemistry in zeolites: From catalysts to sunscreens." Pure and Applied Chemistry, vol. 79, No. 1, 2007, pp. 1-20.
Lin et al., "A study of purified montmorillonite intercalated with 5-fluorouracil as drug carrier." Biomaterials 23 (2002) pp. 1981-1987.
Kawano et al., "Experimental study on the formation of zeolites from obsidian by interaction with NaOH and KOH . . . " Clays and Clay Minerals, vol. 45, No. 3, 1997, pp. 365-377.
Cai et al., "The effect of curing conditions on compression strength and porosity of metakaolin-based geopolymers," Ceram. Eng. Sci. Proc. vol. 34, Iss. 10, 2013, pp. 49-56.
Gupta et al., "Formation of physically stable amorphous drugs by milling with Neusilin." Journal of Pharm Sci, Mar. 2003, 92(3), pp. 536-551.
Petermann et al., "Alkali-activated Geopolymers: A Literature Review", Air Force Research Laboratory, Jul. 2010.
The James Hutton Institute, "Halloysite and Kaolinite" www.claysandminerals.com/materials/halloysite, printed Dec. 23, 2014.
Lin, Petroleum Engineering Construction, Oct. 2005, vol. 31, No. 5, pp. 9-11 (with English abstract).
Cai, B. et al., "Development and evaluation of a tampering resistant transdermal fentanyl patch." Int. J. Pharm., 488 (2015) 102-107.
Mostafa, N.Y., "Characterization, thermal stability and sintering of hydroxyapatite powders prepared by different routes." Mater. Chem. Phys., 94 (2005) 333-341.
Cai, B. et al., "Bioceramic microneedles with flexible and self-swelling substrate." Eur. J. Pharm. Biopharm., 94 (2015) 404-410.
Cai, B., et al. "Self-setting bioceramic microscopic protrusions for transdermal drug delivery." J. Mater. Chem. B., 2014, 2, 5992-5998.

(56) References Cited

OTHER PUBLICATIONS

Figiel, P., et al., "Properties of Alumina Ceramics Obtained by Conventional and Non-conventional Methods for Sintering Ceramics." JAMME, 2011, 48, 29-34.

Martindale: The Complete Drug Reference, "Analgesics Anti-Inflammatory Drugs and Antipyretics." Pharm. Press, 35th ed. 2007, 90.

Wagh, A., "Chemically Bonded Phosphate Ceramics," Elsevier Ltd. Argonne National Laboratories, 2004, Sec. 1.1, 1-2.

Aulton, M.E., "Aulton's Pharmaceutics", 3rd ed., 2010, pp. 4-7 and 483-485.

Banga, "Microporation applications for enhancing drug delivery", Expert Opinion Drug Delivery, 2009, vol. 6, No. 4, pp. 343-354.

Davidovits, "30 Years of Successes and Failures in Geopolymer Applications." Geopolymer 2002 Conference, Oct 2002, pp. 1-16.

DURAGESIC® Information Sheet, Janssen Pharmaceutical, Inc. 2009, revised 2012, 11 pages.

Forsgren et al., "A ceramic drug delivery vehicle for oral administration of highly potent opioids", J. Pharm. Sci. 2010, vol. 99, No. 1, pp. 219-226.

Jämstorp et al., "Mechanically strong geopolymers offer new possibilities in treatment of chronic pain", J. Control. Release, 2010, vol. 146, pp. 370-377.

Rowe et al.. "Handbook of Pharmaceutical Excipients" 6th ed.. 2009, pp. 525-533 and 581-585.

* cited by examiner

COMPOSITION FOR SUSTAINED DRUG DELIVERY COMPRISING GEOPOLYMERIC BINDER

FIELD OF THE INVENTION

This invention relates to new, non-abusable pharmaceutical compositions (drug delivery systems; DDSs) that provide for the controlled release of active pharmaceutical ingredients (APIs), such as opioid analgesics, in e.g. the gastrointestinal tract. The invention also relates to methods of manufacturing such DDSs.

BACKGROUND

The listing or discussion of an apparently prior-published document in this specification should not necessarily be taken as an acknowledgement that the document is part of the state of the art or is common general knowledge.

Opioids are widely used in medicine as analgesics, for example in the treatment of patients with severe pain, chronic pain, or to manage pain after surgery. Indeed, it is presently accepted that, in the palliation of more severe pain, no more effective therapeutic agents exist.

The term "opioid" is typically used to describe an API that activates opioid receptors, which are found in the brain, the spinal cord and the gut. Three classes of opioids exist:

(a) naturally-occurring opium alkaloids. These include morphine and codeine;
(b) compounds that are similar in their chemical structure to the naturally-occurring opium alkaloids. These so-called semi-synthetics are produced by chemical modification of the latter and include the likes of diamorphine (heroin), oxycodone and hydrocodone; and
(c) truly synthetic compounds such as fentanyl and methadone. Such compounds may be completely different in terms of their chemical structures to the naturally-occurring compounds.

Of the three major classes of opioid receptors ($\mu$, $\kappa$ and $\delta$), opioids' analgesic and sedative properties mainly derives from agonism at the $\mu$ receptor.

Opioid analgesics are used to treat the severe, chronic pain of terminal cancer, often in combination with non-steroid anti-inflammatory drugs (NSAIDs), as well as acute pain (e.g. during recovery from surgery). Further, their use is increasing in the management of chronic, non-malignant pain.

Optimal management of chronic pain requires around-the-clock coverage. In this respect, opioid-requiring cancer patients are usually given slow-release opiates (slow-release morphine, oxycodone or ketobemidone, or transdermal fentanyl). DDSs that are capable of providing a sustained release of such APIs allow the patient to obtain this baseline analgesia with a minimal number of doses per day. This in turn improves patient compliance and minimizes interference with the individual's lifestyle and therefore quality of life.

Transdermal fentanyl DDSs comprise patches (e.g. DURAGESIC®) that are applied to the skin to deliver that potent opioid analgesic, which is slowly absorbed through the skin into systemic circulation. Pain may be relieved for up to three days from a single patch application.

However, such patches do not provide for a constant plasma level of API over the entire application period. This defect is an inevitable consequence of the fact that transdermal administration of fentanyl gives rise to the formation of a fentanyl depot in skin tissue. Serum fentanyl concentrations increase gradually following initial application of a patch, generally levelling off between 12 and 24 hours before reaching a saturation point, whereafter absorption of API remains relatively constant, with some fluctuation, for the remainder of the 72-hour application period.

Furthermore, firstly, in the design of sustained release DDSs with extremely potent APIs, such as opioids, the risk for "dose dumping" has to be eliminated in view of the risk of severe and, on occasions, lethal side effects. Secondly, a perennial problem with potent opioid analgesics such as fentanyl is one of abuse by drug addicts. Addicts normally abuse DDSs by one or more of the following processes:

(i) extracting a large quantity of API from that DDS using acid and/or alcohol into solution, which is then injected intravenously. With most commercially-available DDSs, this can be done relatively easily, which renders them unsafe or "abusable";
(ii) heating (and then smoking);
(iii) crushing of tablet (and then snorting); and/or
(iv) in the case of a patch, making a tea (and then drinking).

Thus, there is a clear unmet clinical need for an effective DDS that is capable of treating e.g. severe pain via a sustained release of APIs (such as opioid analgesics), whilst at the same time minimising the possibility of dose dumping and/or abuse by addicts.

Ceramics are becoming increasingly useful to the medical world, in view of the fact they are durable and stable enough to withstand the corrosive effect of body fluids.

For example, surgeons use bioceramic materials for repair and replacement of human hips, knees, and other body parts. Ceramics also are being used to replace diseased heart valves. When used in the human body as implants or even as coatings to metal replacements, ceramic materials can stimulate bone growth, promote tissue formation and provide protection from the immune system. Dental applications include the use of ceramics for tooth replacement implants and braces.

Ceramics are also known to be of potential use as fillers or carriers in controlled-release DDSs. See, for example, EP 947 489 A, U.S. Pat. No. 5,318,779, WO 2008/118096, Lasserre and Bajpai, *Critical Reviews in Therapeutic Drug Carrier Systems*, 15, 1 (1998), Byrne and Deasy, *Journal of Microencapsulation*, 22, 423 (2005) and Levis and Deasy, *Int. J. Pharm.*, 253, 145 (2003).

In particular, Rimoli et al, *J. Biomed. Mater. Res.*, 87A, 156 (2008), US patent application 2006/0165787 and international patent applications WO 2006/096544, WO 2006/017336 and WO 2008/142572 all disclose various ceramic substances for controlled release of APIs, with the latter two documents being directed in whole or in part to opioid analgesics, with the abuse-resistance being imparted by the ceramic structures' mechanical strength.

Methods employed in these documents typically involve the incorporation of APIs into pre-formed porous ceramic materials comprising e.g. porous halloysite, kaolin, titanium oxide, zirconium oxide, scandium oxide, cerium oxide and yttrium oxide. In this respect, loading of API typically comprises soaking, extrusion-spheronization and/or cryopelletization in the prior art. Ceramic carriers are also optionally mixed with traditional excipients to form tablets or the like. It is known to be difficult to infuse drug into a pre-formed porous ceramic structure. Indeed, in the case of opioids, it is considered that such API-incorporation methodology will not enable the loading of sufficient API to provide appropriate doses for effective therapeutic pain management, over a prolonged time, given that infusion of API into preformed pores is a difficult thing to do.

In WO 2008/142572, drugs are incorporated during the formation of a ceramic carrier using chemically bonded ceramics, such as calcium aluminate or calcium silicate. Although this leads to a higher amount of drug incorporation than is typically the case for preformed ceramic materials, the mechanical strength and the chemical stability of the ceramic structures described in WO 2008/142572 is, relatively speaking, limited, especially in acidic conditions.

There is thus a presently unmet clinical need for a DDS that imparts sustained release of potent APIs over extended periods of time combined with a low risk of dose dumping and/or drug diversion (abuse).

DISCLOSURE OF THE INVENTION

According to the invention, there is provided a sustained release DDS in which an API, or a pharmaceutically acceptable salt thereof, is combined with a geopolymeric binder, preferably during the formation of the latter, which DDSs are referred to hereinafter together as "the DDSs of the invention".

The term "sustained-release" is employed herein synonymously with the term "controlled-release", and will be understood by the skilled person to include DDSs that provide, and/or are adapted to provide, for a "sustained", a "prolonged" and/or an "extended" release of API (in which API is released at a sufficiently retarded rate to produce a therapeutic response over a required period of time).

The term "geopolymer" will be understood by those skilled in the art to include or mean any material selected from the class of synthetic or natural aluminosilicate materials which may be formed by reaction of an aluminosilicate precursor material (preferably in the form of a powder) with an aqueous alkaline liquid (e.g. solution), preferably in the presence of a source of silica.

The term "source of silica" will be understood to include any form of a silicon oxide, such as $SiO_2$, including a silicate. The skilled person with appreciate that silica may be manufactured in several forms, including glass, crystal, gel, aerogel, fumed silica (or pyrogenic silica) and colloidal silica (e.g. Aerosil).

Suitable aluminosilicate precursor materials are typically (but not necessarily) crystalline in their nature include kaolin, dickite, halloysite, nacrite, zeolites, illite, preferably dehydroxylated zeolite, halloysite or kaolin and, more preferably, metakaolin (i.e. dehydroxylated kaolin). Dehydroxylation (of e.g. kaolin) is preferably performed by calcining (i.e. heating) of hydroxylated aluminosilicate at temperatures above 400° C. For example, metakaolin may be prepared as described by Stevenson and Sagoe-Crentsil in *J. Mater. Sci.*, 40, 2023 (2005) and Zoulgami et al in *Eur. Phys J. AP,* 19, 173 (2002), and/or as described hereinafter. Dehydroxylated aluminosilicate may also be manufactured by condensation of a source of silica and a vapour comprising a source of alumina (e.g. $Al_2O_3$).

Precursor materials may also be manufactured using sol-gel methods, typically leading to nanometer sized amorphous powder (or partly crystalline) precursors of aluminosilicate, as described in Zheng et al in *J. Materials Science,* 44, 3991-3996 (2009).

If provided in the form of a powder, the grain size of the aluminosilicate precursor particles are below about 500 µm, preferably below about 100 µm, more preferred below about 30 µm.

In the formation of geopolymer materials, such precursor materials may be dissolved in an aqueous alkaline solution, for example with a pH value of at least about 12, such as at least about 13. Suitable sources of hydroxide ions include strong inorganic bases, such as alkali or alkaline earth metal (e.g. Ba, Mg or, more preferably, Ca or, especially Na or K, or combinations thereof) hydroxides (e.g. sodium hydroxide). The molar ratio of metal cation to water can vary between about 1:100 and about 10:1, preferably between about 1:20 and about 1:2.

A source of silica (e.g. a silicate, such as $SiO_2$) is preferably added to the reaction mixture by some means. For example, the aqueous alkaline liquid may comprise $SiO_2$, forming what is often referred to as waterglass, i.e. a sodium silicate solution. In such instances, the amount $SiO_2$ to water in the liquid is preferably up to about 2:1, more preferably up to about 1:1, and most preferably up to about 1:2. The aqueous liquid may also optionally contain sodium aluminate.

Silicate (and/or alumina) may alternatively be added to the optionally powdered aluminosilicate pre cursor material, preferably as fume silica (microsilica; AEROSIL® silica). The amount that may added is preferably up to about 30 wt %, more preferably up to about 5 wt % of the aluminosilicate precursor.

The presence of free hydroxide ions in this intermediate alkaline mixture, causes aluminium and silicon atoms from the source material(s) to be dissolved. The geopolymer materials may then be formed by allowing the resultant mixture to set (cure or harden), during which process the aluminium and silicon atoms from the source materials reorientate to form a hard (and at least largely) amorphous geopolymeric material. Curing may be performed at room temperature, at elevated temperature or at reduced temperature, for example at around or just above ambient temperature (e.g. between about 20° C. and about 90° C. (e.g. 50° C.), such as around 40° C.). The hardening may also be performed in any atmosphere, humidity or pressure (e.g. under vacuum or otherwise). The resultant inorganic polymer network is in general a highly-coordinated 3-dimensional aluminosilicate gel, with the negative charges on tetrahedral $Al^{3+}$ sites charge-balanced by alkali metal cations.

In this respect, in a preferred embodiment, the DDS may be formed by mixing a powder comprising the aluminosilicate precursor and an aqueous liquid (e.g. solution) comprising water, a source of hydroxide ions as described hereinbefore and the source of silica (e.g. silicate), to form a paste. The ratio of the liquid to the powder is preferably between about 0.2 and about 20 (w/w), more preferably between about 0.3 and about 10 (w/w).

In the process for formation of DDSs of the invention, API may be added to preformed geopolymer, but is preferably included in the geopolymeric binder during the formation of the latter. Thus, the aqueous alkaline liquid may contain API, preferably up to about 30 wt %, more preferably up to about 10 wt %, as calculated on the sum of all the ingredients that are included in that liquid. Alternatively, API may be added to the aluminosilicate precursor component prior to mixing with the aqueous alkaline liquid. The amount of API added to the precursor component may be up to about 70 wt %, and preferably between about 3 and about 10 wt %, of the total powder weight.

Curing may be performed by allowing the paste to harden into any given shape, e.g. blocks, pellets, granules or a powder.

In this respect, the paste may be transferred into moulds and left to set as pellets/granules or alternatively (e.g. preferably) pellets/granules may be manufactured using an appropriate extrusion-spheronization technique. Here, the formed paste (powder and liquid mixture) may be extruded through an orifice. The size of the orifice may be from about 10 μm up to about 30 mm, preferably from about 100 μm to about 1 mm. The formed extrudate may then be placed in a spheronizer, which is typically a vertical hollow cylinder with a horizontal rotating disk located inside. When the disk is spun, the extrudate is broken into uniform lengths and gradually formed into spherical pellets, which may then be left to harden as described hereinbefore.

Suitable pellet/granule sizes are in the range of about 0.05 mm to about 3.0 mm (e.g. about 2.0 mm, such as about 1.7 mm), and preferably about 0.1 mm (e.g. about 0.2 mm) to about 1.6 mm (e.g. about 1.5 mm), such as about 1 mm.

The DDSs of the invention may further comprise one or more commonly-employed pharmaceutical excipients. Suitable excipients include inactive substances that are typically used as a carrier for the APIs in medications. Suitable excipients also include those that are employed in the pharmaceutical arts to bulk up DDSs that employ very potent APIs, to allow for convenient and accurate dosing. Alternatively, excipients may also be employed in manufacturing processes of the DDSs of the invention to aid in the handling of the API concerned.

In this respect, pharmaceutically-acceptable excipients include filler particles, by which we include particles that do not take part in the chemical reaction during which the geopolymeric binder-based DDS of the invention is formed. Such filler particles may be added as ballast and/or may provide the DDS with functionality. Non-limiting examples include: zirconium dioxide and barium sulfate to increase radio-opacity, which may be added to smaller particles (e.g. milled) DDS according to the present invention (including the API). DDSs according to the invention may thus comprise particles comprising:

(i) inert fillers, such as those mentioned hereinbefore;
(ii) DDS including API; and/or
(iii) other API-loaded porous ceramic particles (e.g. for sustained release) bound together by geopolymer.

DDSs of the invention may alternatively be milled to a fine powder, preferably with a powder grain size of below about 100 μm, and more preferably below about 20 μm. Milling is optionally performed using ball-milling, planetary ball-milling, jet milling or a combination thereof. The amount of added filler particles may be up to about 80 wt %, preferably up to about 40 wt % of the aluminosilicate precursor weight.

The alkaline liquid or aluminosilicate precursor may also optionally contain bulking agents, porogens, dispersion agents or gelating agents to control the rheology or the amount of liquid in the geopolymer. The total amount of such excipients is limited to about 20 wt % of the total weight of the precursor and liquid combined. Non-limiting examples of such excipients include polycarboxylic acids, cellulose, polyvinylalchol, polyvinylpyrrolidone, starch, nitrilotriacetic acid (NTA), polyacrylic acids, PEG, sorbitol, mannitol and combinations thereof.

Additional pharmaceutically-acceptable excipients include carbohydrates and inorganic salts such as sodium chloride, calcium phosphates, calcium carbonate. Such additional materials are preferably added to the aluminosilicate precursor component. Calcium silicate and calcium aluminate may also be added to the aluminosilicate precursor component.

DDSs of the invention may also comprise film-forming agents. The term "film-forming agent" refers to a substance that is capable of forming a film over (or within), or coating over, another substance (which may be in particulate form).

It is preferred that the film-forming agent is a material that is capable of providing a sustained-release, delayed-release or, preferably, enteric-release coating (i.e. an enteric coating material). Substances that are capable of providing an enteric coating are thus those that may be employed in peroral DDSs as a barrier to prevent or minimise release of API prior to such DDSs reaching the small intestine.

In this respect, it is preferred that the film-forming agent is a polymer. Examples of polymers that may be employed as film-forming agents include, without limitation: alkylcellulose polymers (e.g. ethylcellulose polymers), and acrylic polymers (e.g. acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly(methyl methacryate), poly(methacrylic acid) (anhydride), methyl methacrylate, polymethacrylate, methyl methacrylate copolymer, poly(methyl methacrylate), poly(methyl methacrylate) copolymer, polyacryamide, aminoalkyl methacrylate copolymer, poly(methacrylic acid anhydride), and glycidyl methacrylate copolymers). The polymer may also be a mixture of polymers. Typically, the molecular weight (weight average and/or number average) of the polymer is 1,000 to 10,000,000, 10,000 to 1,000,000, preferably 50,000 to 500,000 g/mol, as measured by gel permeation chromatography.

Preferred polymers include the alkyl cellulose polymers and acrylic polymers described herein.

Preferably, the film-forming agent comprises a polymer that exhibits anionic character and/or is weakly acidic (for example that have a pH of less than 7, and preferably less than 5).

The most preferred polymer includes that marketed under the trademark Kollicoat®. Kollicoat® comprises a copolymer derived from methacrylic acid and ethyl acrylate. Kollicoat® MAE 30 DP (BASF) is a copolymer of methacrylic acid/ethyl acrylate (1:1), and is available as an aqueous dispersion or powder. Other polymers that may be mentioned include those marketed under the trademark Eudragit®, which are neutral methacrylic polymers with acid or alkaline groups.

DDSs of the invention may also comprise a pelletisation aid material. A pelletisation aid material may be defined as a material that is capable of controlling the distribution of granulating liquid through the wet powder mass during pelletisation and to modify the rheological properties in the mixture. Suitable pelletisation aid materials include hydroxypropylmethylcellulose (HPMC), hydroxyethylcellulose (HEC) and, preferably, microcrystalline cellulose. If present, the pelletisation aid material is preferably employed in an amount of between 0.5 and 50% by weight based upon the total weight of the DDS. A preferred range is from 1 to 20%, such as from about 2.0 to about 12% (e.g. about 10%) by weight.

After hardening the DDS may contain unreacted aluminosilicate mineral but consists essentially of a geopolymeric binder with the general composition:

$M_2O * xSiO_2 * yAl_2O_3 * zH_2O$ wherein
M is an alkali metal cation, preferably Na or K;
x is in the range of 0.1-300, preferably 1-50;

y is in the range of 0.1-100, preferably 0.5-10; and
z is in the range of 0.1-100, preferably 1-20.

APIs that may be employed in DDSs of the invention preferably include substances from various pharmacological classes, e.g. antibacterial agents, antihistamines and decongestants, anti-inflammatory agents, antiparasitics, antivirals, local anaesthetics, antifungals, amoebicidals or trichomonocidal agents, analgesics, antianxiety agents, anticlotting agents, antiarthritics, antiasthmatics, anticoagulants, anticonvulsants, antidepressants, antidiabetics, antiglaucoma agents, antimalarials, antimicrobials, antineoplastics, antiobesity agents, antipsychotics, antihypertensives, auto-immune disorder agents, anti-impotence agents, anti-Parkinsonism agents, anti-Alzheimer's agents, antipyretics, anticholinergics, anti-ulcer agents, blood-glucose-lowering agents, bronchodilators, central nervous system agents, cardiovascular agents, cognitive enhancers, contraceptives, cholesterol-reducing agents, agents that act against dyslipidermia, cytostatics, diuretics, germicidials, H2 blockers, hormonal agents, anti-hormonical agents, hypnotic agents, inotropics, muscle relaxants, muscle contractants, physical energizers, sedatives, sympathomimetics, vasodilators, vasoconstrictors, tranquilizers, electrolyte supplements, vitamins, uricosurics, cardiac glycosides, membrane efflux inhibitors, membrane transport protein inhibitors, expectorants, purgatives, contrast materials, radiopharmaceuticals, imaging agents, peptides, enzymes, growth factors, vaccines and mineral trace elements. Other API substances include proton pump inhibitors.

APIs that may be employed in DDSs of the invention preferably include any that are open to abuse potential, such as those that are useful in the treatment of acute or chronic pain, attention deficit hyperactivity disorders (ADHD), anxiety and sleep disorders, as well as growth hormones (e.g. erythropoietin), anabolic steroids, etc. A full list of potentially abusable substances may be found by the skilled person, for example on the weblink http://www.deadiversion.usdoj.gov/schedules/alpha/alphabetical.htm.

Non-opioid APIs that may be specifically mentioned include psychostimulants, such as modafinil, amphetamine, dextroamphetamine, methamphetamine and hydroxyamphethamine and, more preferably, methylfenidate; benzodiazepines, such as bromazepam, camazepam, chlordiazepoxide, clotiazepam, cloxazepam, delorazepam, estazolam, fludiazepam, flurazepam, halazepam, haloxazepam, ketazolam, lormetazepam, medazepam, nimetazepam, nordiazepam, oxazolam, pinazepam, prazepam, temazepam, tetrazepam and, more preferably, alprazolam, clonazepam, diazepam, flunitrazepam, lorazepam, midazolam, nitrazepam, oxazepam and triazolam; and other, non-benzodiazepine sedatives (e.g. short-acting hypnotics), such as zaleplon, zolpidem, zopiclone and eszopiclone.

DDSs of the invention may also find utility in the formulation of APIs where crushing of a tablet may put the patient at risk, or may increase the risk for adverse effects and/or an unpleasant taste. That is to say, those APIs where avoidance of one or more of the following is desirable:
  i) a tablet being chewed before being swallowed;
  ii) accidental destruction during passage through the gastrointestinal tract;
  iii) release of API content as a consequence of concomitant intake of, for instance, alcoholic beverages, which may destroy the controlled release functionality of the DDS; and/or
  iv) ex vivo tampering, i.e. crushing for subsequent abuse (vide infra), or for ease of subsequent swallowing, which may result in destruction of the functionality of the formulated API.

Such APIs will be well known to the skilled person, but may also be found for example on the weblink http://www.ismp.org/Tools/DoNotCrush.pdf. Such APIs include those that are used for the treatment of a variety of disorders where slow release DDSs are beneficial, including APIs that are employed in the treatment of cardiovascular diseases (hypertension, heart failure), diabetes, asthma, CNS disorders and urogenital disorders, as well as antibiotics.

However, preferred APIs that may be employed in DDSs of the invention include opioid analgesics. The term "opioid analgesic" will be understood by the skilled person to include any substance, whether naturally-occurring or synthetic, with opioid or morphine-like properties and/or which binds to opioid receptors, particularly the µ-opioid receptor, having at least partial agonist activity, thereby capable of producing an analgesic effect. The problems of potential DDS tampering and API extraction by drug addicts are particularly prominent with opioids.

Opioid analgesics that may be mentioned include opium derivatives and the opiates, including the naturally-occurring phenanthrenes in opium (such as morphine, codeine, thebaine and Diels-Alder adducts thereof) and semisynthetic derivatives of the opium compounds (such as diamorphine, hydromorphone, oxymorphone, hydrocodone, oxycodone, etorphine, nicomorphine, hydrocodeine, dihydrocodeine, metopon, normorphine and N-(2-phenylethyl)normorphine). Other opioid analgesics that may be mentioned include fully synthetic compounds with opioid or morphine-like properties, including morphinan derivatives (such as racemorphan, levorphanol, dextromethorphan, levallorphan, cyclorphan, butorphanol and nalbufine); benzomorphan derivatives (such as cyclazocine, pentazocine and phenazocine); phenylpiperidines (such as pethidine (meperidine), fentanyl, alfentanil, sufentanil, remifentanil, ketobemidone, carfentanyl, anileridine, piminodine, ethoheptazine, alphaprodine, betaprodine, 1-methyl-4-phenyl-1,2,3,6-tetrahydropyridine (MPTP), diphenoxylate and loperamide), phenylheptamines or "open chain" compounds (such as methadone, isomethadone, propoxyphene and levomethadyl acetate hydrochloride (LAAM)); diphenylpropylamine derivatives (such as dextromoramide, piritramide, bezitramide and dextropropoxyphene); mixed agonists/antagonists (such as buprenorphine, nalorphine and oxilorphan) and other opioids (such as tilidine, tramadol and dezocine). Further opioid analgesics that may be mentioned include allylprodine, benzylmorphine, clonitazene, desomorphine, diampromide, dihydromorphine, dimenoxadol, dimepheptanol, dimethylthiambutene, dioxaphetyl butyrate, dipipanone, eptazocine, ethylmethylthiambutene, ethylmorphine, etonitazene, hydroxypethidine, levophenacylmorphan, lofentanil, meptazinol, metazocine, myrophine, narceine, norpipanone, papvreturn, phenadoxone, phenomorphan, phenoperidine and propiram.

Non limiting examples of opioid analgesics include morphine, meperidine, fentanyl, hydromorphone, oxymorphone, oxycodone, hydrocodone, methadone, propoxyphene, pentazocine, levorphanol and codeine. Other APIs that may be mentioned include, naloxone and acetaminophen and combinations of these with any of the opioid analgesics listed above or below.

More preferred opioid analgesics include buprenorphine, alfentanil, sufentanil, remifentanil and, particularly, fentanyl.

APIs listed above may be formulated in DDS according to the invention in any specific combination.

APIs may be employed in salt form or any other suitable form, such as e.g. a complex, solvate or prodrug thereof, or in any physical form such as, e.g., in an amorphous state, as crystalline or part-crystalline material, as co-crystals, or in a polymorphous form or, if relevant, in any stereoisomeric form including any enantiomeric, diastereomeric or racemic form, or a combination of any of the above.

Pharmaceutically-acceptable salts of APIs that may be mentioned include acid addition salts and base addition salts. Such salts may be formed by conventional means, for example by reaction of a free acid or a free base form of an API with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of API in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

DDSs of the invention may possess one or more of the following properties:

(a) acid resistance, a necessary attribute for the DDS to possess when passing through the stomach following oral administration. In this respect, DDSs of the invention may show an insignificant degree (e.g. less than 1%) of chemical degradation or decomposition in aqueous acid milieu (at pH values between about 0.1 and about of 4.0) at temperatures in excess of room temperature (e.g. up to about 50° C.);

(b) general physico-chemical stability under normal storage conditions, including temperatures of between about minus 80 and about plus 50° C. (preferably between about 0 and about 40° C. and more preferably room temperatures, such as about 15 to about 30° C.), pressures of between about 0.1 and about 2 bars (preferably at atmospheric pressure), relative humidities of between about 5 and about 95% (preferably about 10 to about 75%), and/or exposure to about 460 lux of UV/visible light, for prolonged periods (i.e. greater than or equal to six months). Under such conditions, DDSs of the invention may be found to be less than about 5%, such as less than about 1% chemically degraded/decomposed, as above;

(c) particularly importantly when the API that is employed is an opioid analgesic, general physico-chemical stability under acidic, alkaline and/or alcoholic (e.g. ethanolic) conditions at room temperature and/or under at elevated temperatures (e.g. up to about 100° C.), which may result in less than about 15% degradation, so avoiding the possibility of deliberate ex vivo extraction of API for intended abuse (e.g. by acid or alcohol extraction, followed by injection, or heating a DDS of the invention and then an opioid addict inhaling the vapour or smoke that is given off); and (d) again, particularly importantly when the API that is employed is an opioid analgesic, general physical stability, for example with a high mechanical impact strength, so reducing the possibility of mechanical grinding or milling with a view to extraction of API as defined in (c) above, or by an opioid addict sniffing a resultant powder directly.

With reference to (d) above, it is preferred in this respect that DDSs of the invention exhibit a compressive strength of greater than about 10 MPa, such as 50 MPa, which is high enough to withstand breakdown of the material at the microstructure level, i.e. of less than about 200 μm.

In this respect, we also include that DDSs of the invention maintain their overall integrity (e.g. shape, size, porosity, etc) when a force of about 1 kg-force/cm$^2$ (9 newtons/cm$^2$), such as about 5 kg-force/cm$^2$ (45 newtons/cm$^2$), for example about 7.5 kg-force/cm$^2$, e.g. about 10.0 kg-force/cm$^2$, preferably about 15 kg-force/cm$^2$, more preferably about 20 kg-force/cm$^2$, for example about 50 kg-force/cm$^2$, especially about 100 kg-force/cm$^2$ or even about 125 kg-force/cm$^2$ (1125 newtons/cm$^2$) is applied using routine mechanical strength testing techniques known to the skilled person (for example using a so-called "compression test" or "diametral compression test", employing a suitable instrument, such as that produced by Instron (the "Instron Test", in which a specimen is compressed, deformation at various loads is recorded, compressive stress and strain are calculated and plotted as a stress-strain diagram which is used to determine elastic limit, proportional limit, yield point, yield strength and (for some materials) compressive strength)). When the structure of the DDS is particulate, at least about 40% (e.g. at least about 50%, such as at least about 60% preferably, at least about 75%, and more preferably at least about 90%) of the particles (whether primary or secondary particles) maintain their integrity under these conditions.

DDSs of the invention may be incorporated into various kinds of pharmaceutical preparations using standard techniques (see, for example, Lachman et al, "*The Theory and Practice of Industrial Pharmacy*", Lea & Febiger, 3$^{rd}$ edition (1986) and "*Remington: The Science and Practice of Pharmacy*", Gennaro (ed.), Philadelphia College of Pharmacy & Sciences, 19$^{th}$ edition (1995)), for example to form a capsule, a powder or a tablet.

The DDSs of the invention are preferably administered perorally to the gastrointestinal tract and may provide for controlled release of API in the stomach and/or, preferably, the intestinal system.

DDS of the invention may also be presented in the form of buccal or sublingual tablets, or may even be designed for topical application.

Pharmaceutical preparations comprising DDSs of the invention contain a pharmacologically effective amount of the API. By "pharmacologically effective amount", we refer to an amount of API, which is capable of conferring a desired therapeutic effect on a treated patient, whether administered alone or in combination with another API. Such an effect may be objective (i.e. measurable by some test or marker) or subjective (i.e. the subject gives an indication of, or feels, an effect).

More preferred DDSs of the invention may be adapted (for example as described herein) to provide a sufficient dose of API over the dosing interval (irrespective of the number of doses per unit time) to produce a desired therapeutic effect.

The amounts of APIs that may be employed in DDSs of the invention may thus be determined by the physician, or the skilled person, in relation to what will be most suitable for an individual patient. This is likely to vary with the route of administration, the type and severity of the condition that is to be treated, as well as the age, weight, sex, renal function, hepatic function and response of the particular patient to be treated.

Suitable dosages of API in one oral delivery unit (e.g. one tablet) may be below 1 g, preferably below 100 mg and above 1 μg.

When DDSs of the invention comprise opioid analgesics, appropriate pharmacologically effective amounts of such opioid analgesic compounds include those that are capable of producing (e.g. sustained) relief of pain when administered perorally. Thus, the total amount of opioid analgesic API that may be employed in a DDS of the invention will depend upon the nature of the relevant API that is employed, but may be in the range of about 0.0005%, such as about 0.1% (e.g. about 1%, such as about 2%) to about 20%, such as about 10%, for example about 7%, by weight based upon the total weight of the DDS. The amount of this API may also be expressed as the amount in a unit dosage form. In such a case, the amount of opioid analgesic API that may be present may be sufficient to provide a dose per unit dosage form that is in the range of between about 1 μg (e.g. about 5 μg) and about 50 mg (e.g. about 15 mg, such as about 10 mg).

The above-mentioned dosages are exemplary of the average case; there can, of course, be individual instances where higher or lower dosage ranges are merited, and such are within the scope of this invention.

DDSs of the invention comprising opioid analgesics are useful in the treatment of pain, particularly severe and/or chronic pain. According to a further aspect of the invention there is provided a method of treatment of pain which method comprises administration of a DDS of the invention to a person suffering from, or susceptible to, such a condition.

For the avoidance of doubt, by "treatment" we include the therapeutic treatment, as well as the symptomatic treatment, the prophylaxis, or the diagnosis, of the condition.

We have advantageously found that DDSs of the invention provide for release of API that is substantially uniform and/or nearly constant over an extended period of time. In one embodiment, a nearly constant rate of release can vary over a dose interval from about 6 hours to about 2 days. Constant release may further be defined as a DDS being capable of maintaining a steady state concentration in a body fluid not deviating more than about 20% (e.g. about 10%) from the mean value during the dose interval. The release rate may be maintained over a long time period, corresponding approximately to the passage of time taken between initial oral administration of a DDS of the invention and excretion of the carrier material from the body, such as between about 5 and about 24 (such as about 15) hours.

DDSs of the invention possess the advantage of the avoidance and/or reduction of the risk of either dose dumping (i.e. the involuntary release), or equally importantly the deliberate ex vivo extraction, of the majority (e.g. greater than about 50%, such as about 60%, for example about 70% and in particular about 80%) of the dose of the API(s) that is/are initially within a DDS of the invention, either in vivo (i.e. when a DDS of the invention is administered to a patient) or ex vivo (i.e. into another medium outside the body), within a timeframe that is likely to give rise to undesirable consequences, such as adverse pharmacological effects (for example when such release occurs in vivo in an involuntary sense), or the potential for abuse of that API (for example when such release is deliberately effected ex vivo by an individual). Such dose dumping release may for example take place either in vivo or ex vivo within about 3 hours, such as within about 2 hours, for example within about 1 hour, and particularly within about 30 minutes.

DDSs of the invention have the advantage that they provide for improved sustained release properties with minimal risk for severe/lethal side effects (i.e. reduction of dose dumping and/or abuse potential when the API to be employed is abusable, such as an opioid, a benzodiazepine, etc.). The DDSs of the invention may provide protection against intentional mechanical breakdown, e.g. by traditional methods such as crushing, pestle and mortar, hammering etc by having a high compressive strength level at the micro-level material. This protection may be provided by the DDS of the invention as such, and especially when those DDSs are employed in conjunction with a carrier or filler that also possesses high mechanical strength.

DDSs of the invention may also have the advantage that they may be prepared using established pharmaceutical processing methods and may employ materials that are approved for use in foods or pharmaceuticals or of like regulatory status.

DDSs of the invention may also have the advantage that they may be more efficacious than, be less toxic than, be longer acting than, be more potent than, produce fewer side effects than, be more easily absorbed than, and/or have a better pharmacokinetic profile than, and/or have other useful pharmacological, physical, or chemical properties over, DDSs known in the prior art, whether for use in the treatment of pain or otherwise.

Wherever the word "about" is employed herein in the context of dimensions (e.g. values, temperatures, pressures (exerted forces), relative humidities, sizes and weights, particle or grain sizes, pore sizes, timeframes etc.), amounts (e.g. relative amounts (e.g. numbers, ratios or percentages) of particles, individual constituents in a DDS/composition or a component of a DDS/composition and absolute amounts, such as doses of APIs, numbers of particles, etc), deviations (from constants, degrees of degradation, etc) it will be appreciated that such variables are approximate and as such may vary by ±10%, for example ±5% and preferably ±2% (e.g. ±1%) from the numbers specified herein.

BRIEF DESCRIPTION OF THE DRAWINGS

The invention is illustrated by the following examples in which.

EXAMPLES

Example 1

Different geopolymers (see Table 1 below) were prepared by mixing relevant API (fentanyl base (Johnson Matthey MacFarlan & Smith (UK)) or zolpidem tartrate (Cambrex Charles City Inc (USA)); <1 wt %), metakaolin (prepared by heating kaolin (Sigma-Aldrich, Sweden AB) at 800° C. for 2 hours) and different waterglasses (sodium silicate solutions; prepared by mixing different amounts of deionized water with aqueous solutions containing dissolved $SiO_2$ and NaOH) into a homogeneous paste in a glass mortar.

The paste was subsequently transferred to a pellet Teflon®-mould with cylindrically shaped holes with a size of 1.5×1.5 mm (diameter x height). The mould was in turn placed in an oven set to 40° C. for 48 hours to complete geopolymerisation.

TABLE 1

Molar ratios of the different compounds of the samples together with the sample porosities and the API release process diffusion coefficients (Abbrev. Zol = zolpidem sample; Fen = fentanyl sample)

| Sample | Molar Ratio | | | D (pH 6.8)[1] | Porosity $\epsilon^2$ |
|---|---|---|---|---|---|
| | $H_2O/SiO_2$ | $Na_2O/SiO_2$ | Si/Al | [$10^{-9}$ cm²/s] | [%] |
| Zol1 | 2.6 | 0.28 | 1.76 | — | 22 ± 13 |
| Zol2 | 3.4 | 0.28 | 1.76 | — | 21 ± 7 |
| Zol3 | 4.5 | 0.49 | 1.76 | — | 19 ± 6 |
| Zol4 | 5.9 | 0.50 | 1.76 | 45.5 ± 2.3 | 32 ± 6 |
| Zol5 | 3.5 | 0.33 | 1.55 | — | 28 ± 3 |
| Zol6 | 5.5 | 0.44 | 1.55 | 24.3 ± 2.1 | 49 ± 6 |
| Zol7 | 4.3 | 0.33 | 1.32 | 7.8 ± 0.1 | 36 ± 6 |
| Zol8 | 4.5 | 0.42 | 1.32 | 9.6 ± 1.3 | 44 ± 16 |
| Zol9 | 4.3 | 0.28 | 1.06 | 11.1 ± 1.3 | 44 ± 4 |
| Zol10 | 4.3 | 0.33 | 1.06 | 10.1 ± 2.1 | 49 ± 6 |
| Zol11 | 4.5 | 0.49 | 1.06 | 13.3 ± 2.6 | 41 ± 6 |
| Zol12 | 5.9 | 0.49 | 1.06 | 19.4 ± 4.1 | 50 ± 7 |
| Fen3 | 4.5 | 0.49 | 1.77 | — | — |
| Fen5 | 3.6 | 0.33 | 1.55 | — | — |
| Fen8 | 4.6 | 0.42 | 1.32 | 6.1 | — |
| Fen9 | 4.3 | 0.28 | 1.06 | 6.3 | — |
| Fen10 | 4.4 | 0.33 | 1.06 | 2.7 | — |
| Fen11 | 4.5 | 0.50 | 1.06 | 2.2 | — |

[1]The displayed error values represent absolute deviation of diffusion coefficients for 2-3 measurements on Zol pellet samples from different batches. The diffusion coefficients of Fen samples were mainly extracted from measurements performed on pellets from a single batch, but measurements on reformulated DDSs displayed errors less than 7%.
[2]Since the samples contain less than 1% API, the porosities were only measured for the zolpidem-containing samples. The error values represent absolute deviations for 10 consecutive measurements cycles.

The release of API from the relevant pellets was carried out in a USP-2 dissolution bath (Sotax AT 7, Sotax AG, Switzerland) equipped with 200 mL vessels (37° C., 50 rpm). 150 μg of pellets were placed in each vessel and 1 mL liquid was withdrawn from each vessel 8 to 9 times during the time of release. Release measurements were performed in a phosphate buffer at pH 6.8 and in 0.1M HCl (pH 1.0). The concentration of API in the liquid samples was analyzed with a high performance liquid chromatography system (HPLC, Dionex Summit HPLC system, Dionex corp., Sunnyvale, Calif.). 1M HCl was added to the pH 6.8 liquid samples containing fentanyl to stabilize the API in the media prior to HPLC analysis (0.9 mL sample/0.1 mL 1M HCl). The withdrawn pH 1.0 samples containing zolpidem were diluted with 1M NaOH to enable correct chromatography analysis (0.8 mL sample/0.2 mL 1M NaOH).

The compressive strengths of the different DDSs were tested with an Autograph AGS-H universal testing machine (Shimadzu corp., Japan). Eight to ten cylindrical rods of each DDS with the dimensions 6×12 mm (diameter x height) were tested and the averages calculated.

In relation to diffusion coefficients (D), when the initial API content in a rigid delivery vehicle was below the solubility limit of the API and the API dissolution was fast enough to not be a release rate-limiting factor, the API release was assumed to be governed by molecular diffusion through the network of pores of the delivery vehicle. On the assumption that isotropic API release and uniform API loading, whereby the API instantaneously dissolves as the dissolution liquid enters the pore system, the total released API fraction Q as a function of time may be expressed as:

$$Q(t) = 1 - \frac{8}{(HR)^2} \sum_{i,j=1}^{\infty} \frac{1}{\alpha_i^2} \exp(-D\alpha_i^2 t) \frac{1}{\beta_j^2} \exp(-D\beta_j^2 t)$$

Here D is the diffusion coefficient of the API molecules, $\alpha_i = \eta_i/R$, where $\eta_i$ is the i:th zero of the Bessel function $J_0(r)$, $\beta_j = (2j-1)\pi/2H$, where R and H are the radius and height of the cylindrical pellets, respectively.

The porosities of the DDSs were assessed by measurement of the apparent and true densities. The apparent density—i.e. the sample mass divided by the total volume of solid, $V_{tot}$, including all pores, $V_{pores}$—was obtained by averaging the ratio of mass to volume measured with a slide caliper for the pellets. The true density—i.e. the sample mass divided by the skeletal volume of solid—was measured using He pycnometry (AccuPyc 1340, Micromeritics Corp., USA). Helium is assumed to penetrate all pores wider than 0.1-0.2 nm. In effect, the true density, $\rho_t$, of a solid will always be larger than or equal to its apparent density, $\rho_a$. The porosity, $\epsilon$, was hence calculated as:

$$\varepsilon = \frac{V_{pores}}{V_{tot}} = 1 - \frac{\rho_a}{\rho_t}.$$

The zeta potential of crushed and mortared geopolymer was measured with a Zetasizer (Malvern, UK). The potential was measured in aqueous solutions of pH 6.8 and pH 1.0 at 25° C.

Figure 1:
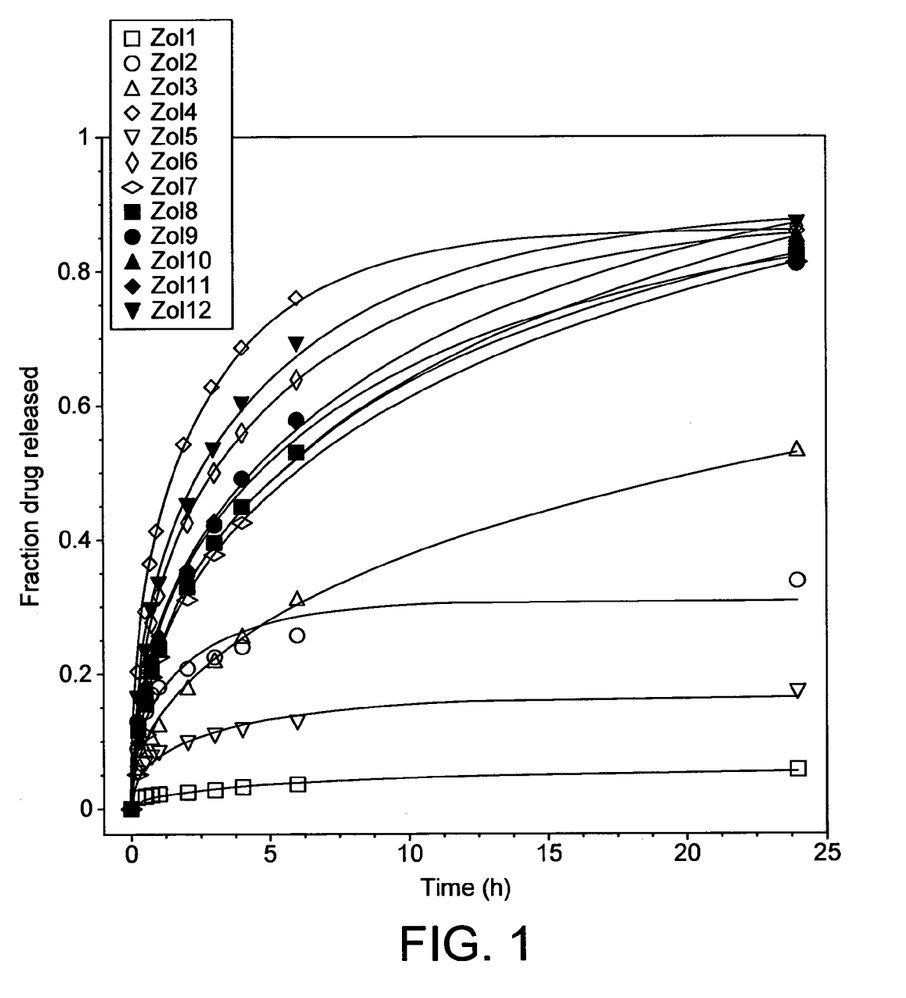
FIGS. 1 and 2 show the release of zolpidem (FIG. 1) and fentanyl (FIG. 2) containing pellets prepared as set out in Example 1 (Table 1) in pH 6.8.
Figure 2:
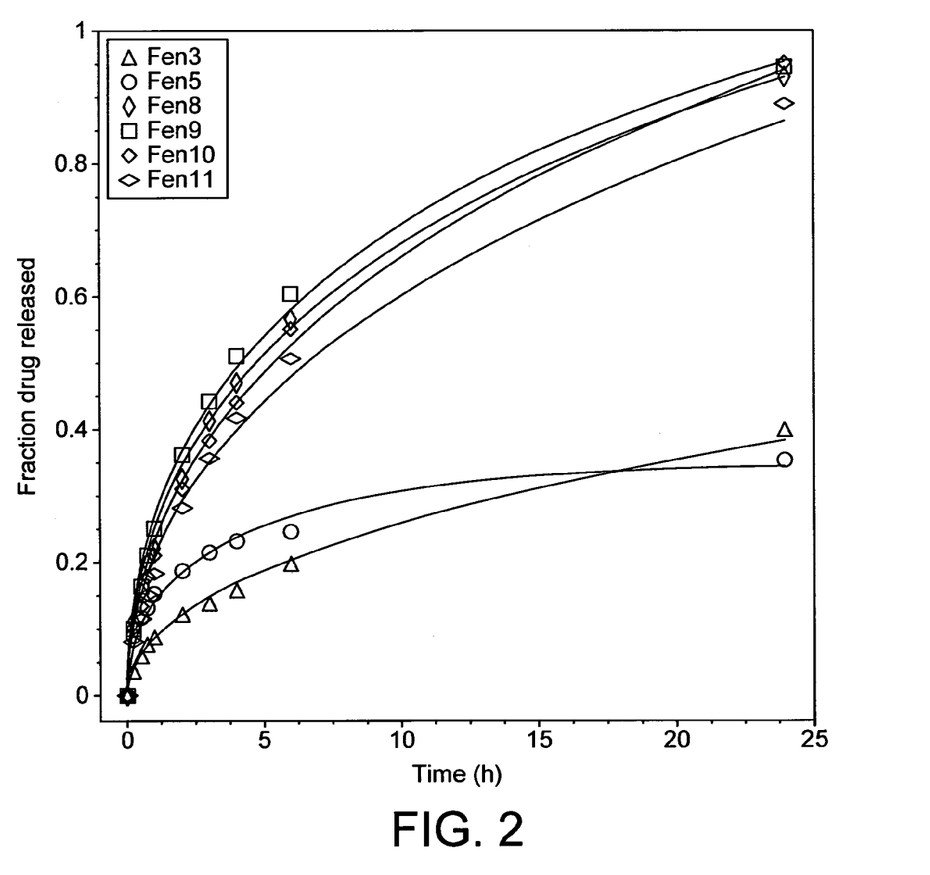

The release of zolpidem (Zol1-12) and fentanyl (Fen3-11) in phosphate buffer (pH 6.8) is shown in FIGS. 1 and 2, respectively. The total amount of API released after 24 hours was approximately the same for all DDSs, namely between about 80 and 95%, with the values for fentanyl being somewhat higher than those for zolpidem, excepting the DDSs that contained higher amounts of silica and simultaneously low amounts of water (high Si/Al ratio and low $H_2O/SiO_2$ ratio, see Table 1 above); viz. Zol1-3, and Zol5 as well as Fen3 and Fen5.

It was found that increasing the amount of water tended to open up the structure and extend the setting time, apparently allowing more time and space for reorganization, i.e. dissolution of the precursor material and re-precipitation of the inorganic polymer structure. This was most markedly seen when comparing the release profiles for Zol3 and Zol4 in FIG. 1. The higher water content of Zol4, cf. Table 1, clearly resulted in a larger amount of released API. The same observation was made when comparing Zol5 and Zol6, and also very slightly for Zol7 and Zol8; an increased amount of water in the structure led to a higher amount of API being released.

It was apparent that an increase in $H_2O/SiO_2$ ratio with a simultaneous decrease in Si/Al ratio shifted the pore distribution maximum from the 5-10 nm range for the Zol1-3 samples to 40-50 nm for the Zol6-7 samples and even out of the measurement range (300 nm) for the applied analysis method for the Zol11-Zol12 samples.

Furthermore, decreasing the Si content as well as increasing the water content clearly increased the porosity, which was assessed by comparing the apparent and skeletal density of the samples (see Table 1). The increase in measured porosity is most likely due to both a larger pore volume and a more interconnected pore structure in the pellets, which allowed the analysis gas to penetrate the structures more effectively.

Figure 3:
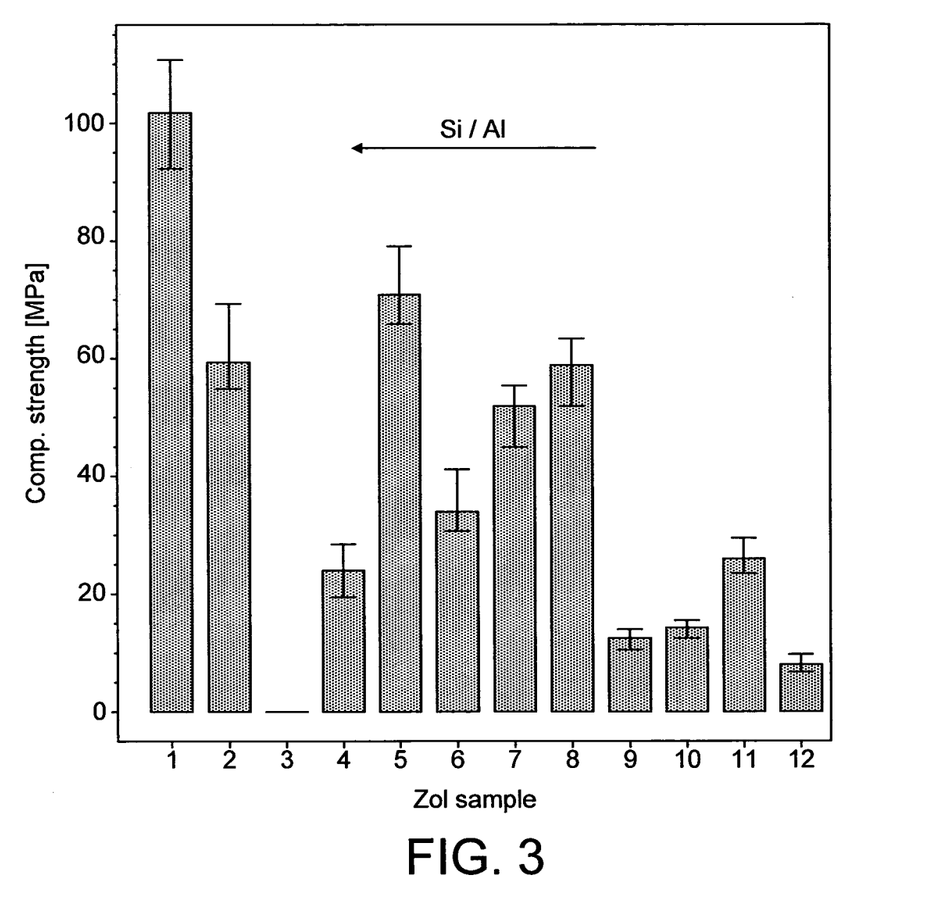
FIG. 3 shows average compression strength of zolpidem containing DDSs (rods) prepared as set out in Example 1. The error bars represent the maximum and minimum compression strength measured for at least 5 compression rods.

FIG. 3 displays the compression strength of twelve different Zolpidem containing samples with compression strengths ranging from 10 to ~100 MPa. It is observed that geopolymer structures with low porosity (high Si/Al ratios, low $H_2O/SiO_2$ ratios) are reported to have the highest strengths. Both size and geometry of the pores as well as the relative pore volume in the structure appears to affect the strength of ceramic materials such as geopolymers. By minimizing the relative pore volume in the structure, the applied load can spread over a larger area and the internal stress can be minimized and, thus, increase the compression strength of the material.

From FIG. 3, it can also be observed that a higher alkali content ($Na_2O/SiO_2$ ratio) rendered a stronger geopolymer structure (e.g. Zol8 stronger than Zol7, Zol11 stronger than Zol10 stronger than Zol9). Unreacted particles may increase the strength of the structure. The higher alkali content may also promote reorganization and densification of the binder phase which in turn also increases the compression strength.

Even though the Zol3 compression rods cracked, the corresponding pellets stayed intact during handling and during the API release measurements. They displayed a more linear release behaviour (FIGS. 1 and 2) of both Zolpidem and Fentanyl (Zol3; Fen3) than did the other DDSs.

The diffusion coefficients, D, of the APIs in the studied geopolymer pellets were extracted to quantify the speed of the API release process (Table 1). The coefficients were obtained by fitting a mathematical solution to the diffusion equation (Fick's second law; see Crank, *The Mathematics of Diffusion* (Clarendon Press, Oxford, 1975)) for a uniform cylindrical body with zero concentration (perfect sink) boundary conditions on all surfaces. In general, the fitting was found to be of very good quality.

The diffusion coefficients proved to be affected by the amount of water used at the preparation of the pellets. A larger amount of water appears to render higher diffusion coefficients and, thus, a more rapid release. The Zolpidem containing DDSs containing the highest amount of water (Zol4, Zol6, and Zol12) released more than 50% of their API within 6 hours.

The release of Fentanyl was somewhat slower than the Zolpidem release (Table 1), although the release rates of the APIs from the different DDSs are almost equal to each other at pH 1.0. There is nevertheless a sustained release of API for at least 4 hours at pH 1.0.

The invention claimed is:

1. A sustained release pharmaceutical composition comprising an active pharmaceutical ingredient, or a pharmaceutically acceptable salt thereof, and an amorphous geopolymeric binder, which composition is in the form of a tablet, blocks, pellets, particles, granules or a powder with a compressive strength of greater than about 10 MPa to about 100 MPa.

2. A composition as claim 1, characterised in that the active pharmaceutical ingredient is combined with the geopolymeric binder during the formation of that binder.

3. A composition as claimed in claim 1, wherein the active pharmaceutical ingredient is an opioid analgesic.

4. A composition as claimed in claim 3, wherein the opioid analgesic is selected from buprenorphine, alfentanil, sufentanil, remifentanil and fentanyl.

5. A composition as claimed in claim 4, wherein the opioid analgesic is fentanyl.

6. A composition as defined in claim 1 for use as a medicine.

7. A composition as defined in claim 3 for use in the treatment of pain.

8. A process for the preparation of a composition as defined in claim 1, which comprises reaction of an aluminosilicate precursor material with an aqueous alkaline liquid, either in the presence of said active pharmaceutical ingredient or salt thereof, or prior to addition of said active pharmaceutical ingredient or salt thereof to the resultant geopolymer.

9. A process as claimed in claim 8, wherein the reaction is performed in the presence of a source of silica.

10. A process as claimed in claim 8 or claim 9, wherein the aluminosilicate precursor material is metakaolin.

11. A process as claimed in claim 8, wherein the aluminosilicate precursor material is in the form of a powder with a grain size that is below about 30 μm.

12. A process as claimed in clam 8, wherein the aqueous alkaline liquid comprises silicate.

13. A process as claimed in claim 8, wherein the geopolymer material is formed by curing at about 40° C.

14. A composition obtainable by a process as defined claim 8.

15. A method of treatment o f pain which comprises administration of a composition as defined in claim 3 to a person suffering from, or susceptible to, such a condition.

16. A sustained release medical composition prepared from:
 (a) powder composition comprising at least an aluminosilicate phase, said phase being optionally selected from the group: kaolin, dickite, halloysite, nacrite, zeolite, lite, and metal aolin;
 (b) water alkaline based liquid; and
 (c) a medical active pharmaceutical ingredient (APT).

17. A tablet produced by a process of:
 (i) a paste of said medical composition according to claim 16, to form a medical composition,
 (ii) granulating said medical composition, and
 (iii) hardening the granulate, and
 (iv) forming a tablet of the hardened medical composition.

18. A method of administrating of a tablet according to claim 17 to a subject in the need thereof.

19. The method of claim 16, wherein said phase being optionally selected from the group consisting of: dehvdroxylated zeolite, halloysite or kaolin.

20. The method of claim 16, wherein said phase being metakaolin.

* * * * *

UNITED STATES PATENT AND TRADEMARK OFFICE
CERTIFICATE OF CORRECTION

PATENT NO.        : 9,486,527 B2
APPLICATION NO.   : 13/319201
DATED             : November 8, 2016
INVENTOR(S)       : Hakan Engquist

Page 1 of 1

It is certified that error appears in the above-identified patent and that said Letters Patent is hereby corrected as shown below:

Column 16, Lines 39-42:
16. (a) "powder composition comprising at least an aluminosilicate phase, said phase being optionally selected from the group: kaolin, dickite, halloysite, nacrite, zeolite, lite, and metal aolin;" should read "powder composition comprising at least an aluminosilicate phase, said phase being optionally selected from the group: kaolin, dickite, halloysite, nacrite, zeolite, Illite, and metakolin;"

Column 16, Lines 46-47:
17. (i) "a paste of said medical composition according to claim 16, to form a medical composition," should read "forming a paste of said medical composition according to Claim 16, to form a medical composition,"

Signed and Sealed this
Twenty-first Day of February, 2017

Michelle K. Lee
*Director of the United States Patent and Trademark Office*